(12) United States Patent
Sydora et al.

(10) Patent No.: US 9,721,070 B2
(45) Date of Patent: Aug. 1, 2017

(54) SELECTIVE OLIGOMERIZATION CATALYSTS AND METHODS OF IDENTIFYING SAME

(71) Applicant: Chevron Phillips Chemical Company LP, The Woodlands, TX (US)

(72) Inventors: Orson L. Sydora, Houston, TX (US); Dawn C. Wiser, Mundelein, IL (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 819 days.

(21) Appl. No.: 14/135,216

(22) Filed: Dec. 19, 2013

(65) Prior Publication Data

US 2015/0178475 A1 Jun. 25, 2015

(51) Int. Cl.
| | |
|---|---|
| G06F 19/00 | (2011.01) |
| C07C 11/02 | (2006.01) |
| C07C 11/107 | (2006.01) |
| C40B 30/02 | (2006.01) |
| B01J 31/18 | (2006.01) |
| B01J 31/24 | (2006.01) |

(52) U.S. Cl.
CPC .......... *G06F 19/703* (2013.01); *B01J 31/189* (2013.01); *B01J 31/24* (2013.01); *B01J 31/2409* (2013.01); *C07C 11/02* (2013.01); *C07C 11/107* (2013.01); *C40B 30/02* (2013.01); *G06F 19/701* (2013.01); *G06F 19/702* (2013.01); *B01J 2231/20* (2013.01); *B01J 2531/62* (2013.01)

(58) Field of Classification Search
CPC .............................. G06F 19/702; G06F 19/703
See application file for complete search history.

(56) References Cited

U.S. PATENT DOCUMENTS

| | | | |
|---|---|---|---|
| 5,856,258 | A | 1/1999 | Marks et al. |
| 6,273,598 | B1 | 8/2001 | Keck et al. |
| 6,653,431 | B1 | 11/2003 | Razavi et al. |
| 6,875,719 | B2 | 4/2005 | Tsai et al. |
| 7,081,536 | B2 | 7/2006 | End et al. |
| 7,554,001 | B2 | 6/2009 | Dixon et al. |
| 8,236,867 | B2 | 8/2012 | Fujita et al. |
| 2012/0172645 | A1 | 7/2012 | Sydora |

FOREIGN PATENT DOCUMENTS

| | | |
|---|---|---|
| JP | 2002193847 A | 7/2002 |
| JP | 2010191529 A | 9/2010 |
| WO | WO 03053891 A1 | 7/2003 |
| WO | 2011082192 A1 | 7/2011 |

OTHER PUBLICATIONS

Occhipinti et al. "Quantitative Structure-Activty Relationships of Ruthenium Catalysts for Olefin Metathesis" Journal of the American Chemical Society, 2006, vol. 128, pp. 6952-6964.*

Sydora et al. "Selective Ethylene Tri-/Tetramerization Catalysts" ACS Catalysis, 2012, vol. 2, pp. 2452-2455.*

Sydora O L et al: "Selective ethylene tri-/tetramerization catalysts" ACS Catalysts, American Chemical Society, US, vol. 2, No. 12, Dec. 7, 2012, pp. 2452-2455.

Occhipinti Giovanni et al: "Quantitative Structure-Activity Relationships of Ruthenium Catalysts for Olefin Metathesis" Journal of the American Chemical Society, American Chemical Society, vol. 128, No, 21, Jan. 1, 2006, pp. 6952-6964.

Koide Y et al: Alumoxanes as Cocatalysts in the Palladium-Catalyzed Copolymerization of Carbon Monoxide and Ethylene: Genesis of a Structure-Activity Relationship, Organometallics, ACS, Washington,DC, vol. 15, No. 9, Jan. 1, 1996, pp. 2213-2226.

Agapie T et al: "Mechanistic Studies of the Ethylene Trimerization Reaction with Chromium-Diphosphine Catalysts: Experimental Evidence for a Mechanism Involving Metallacyclic Intermediates" Journal of the American Chemical Society, American Chemical Society, vol. 2004, No. 126, Jan. 5, 2004, pp. 1304-1305.

Siyang Tang et al: "2D-QSPR/DFT studies of Aryl-substituted PNP-Cr-based Catalyst Systems for Highly Selective Ethylene Oligornerization", Journal of Molecular Modeling, vol. 20, No. 3, Feb. 20, 2014, pp. the whole document.

International Application PCT/US2014/070892 Search Report dated Mar. 9, 2015.

Emrich, Rainer, et al., "The Role of Metallacycles in the Chromium-Catalyzed Trimerization of Ethylene," Organometallics, vol. 16, No. 8, Apr. 15, 1997, pp. 1511-1513, American Chemical Society.

Kim, Sung-Kwan, et al., "Bimetallic Ehtylene Tetramerization Catalysts Derived from Chiral DPPDME Ligands: Synthesis, Structural Characterizations, and Catalytic Performance of [(DPPDME)CrCl3]2 (DPPDME = S,S- and R,R-chiraphos and meso-achiraphos)," Organometallics, vol. 29, No. 22, 2010, pp. 5805-5811, American Chemical Society.

Kozuch, Sebastian, et al., "How to Conceptualize Catalytic Cycles? The Energetic Span Model," Accounts of Chemical Research, vol. 44, No. 2, 2011, pp. 101-110, American Chemical Society.

\* cited by examiner

*Primary Examiner* — Joseph Kosack
(74) *Attorney, Agent, or Firm* — Conley Rose, P.C.; Rodney B. Carroll; Lynda Jolly (57) ABSTRACT

A method comprising obtaining a control catalyst set having a plurality of members each having a control characteristic, wherein the members of the control catalyst set comprise a transition metal and an organic ligand, selecting an intermediate formed during a catalytic cycle of each member of the control catalyst set, geometrically and energetically optimizing a structure of the intermediate, determining one or more characteristics of the geometrically and energetically optimized structure of the intermediate, determining a mathematical relationship between the control characteristic and the one or more characteristics of the geometrically and energetically optimized structure of the intermediate, utilizing the mathematical relationship to identify one or more members of a sample catalyst set having a control characteristic within a desired range, contacting the identified sample catalyst with a reactant under conditions suitable for the formation of product, and recovering the product.

20 Claims, 3 Drawing Sheets

SELECTIVE OLIGOMERIZATION CATALYSTS AND METHODS OF IDENTIFYING SAME

CROSS-REFERENCE TO RELATED APPLICATIONS

Not applicable.

TECHNICAL FIELD

The present disclosure relates to a methodology for the identification of catalysts having some user and/or process desired characteristic. More particularly, the present disclosure relates to methodologies for the selection of catalysts having some user and/or process desired productivity and/or selectivity.

BACKGROUND

Olefin oligomerization catalysts and catalyst systems sometimes lack selectivity to a desired product and/or have a low product yield. Enhancements in preparation methodologies for identifying olefin oligomerization catalysts and catalyst systems having improved productivity and/or selectivity to the desired product may reduce catalyst cost and improve process economics.

SUMMARY

Disclosed herein is a method comprising obtaining a control catalyst set having a plurality of members each having a control characteristic, wherein the members of the control catalyst set comprise a transition metal and an organic ligand; selecting an intermediate formed during a catalytic cycle of each member of the control catalyst set; geometrically and energetically optimizing a structure of the intermediate; determining one or more characteristics of the geometrically and energetically optimized structure of the intermediate; determining a mathematical relationship between the control characteristic and the one or more characteristics of the geometrically and energetically optimized structure of the intermediate; utilizing the mathematical relationship to identify one or more members of a sample catalyst set having a control characteristic within a desired range; contacting the identified sample catalyst with a reactant under conditions suitable for the formation of product; and recovering the product.

Also disclosed herein is a method of generating a predictive model comprising (a) identifying a control catalyst set wherein individual members of the control catalyst set range in a defined characteristic; (b) preparing molecular structures of at least one intermediate in a catalytic cycle of each member of the control catalyst set; (c) geometrically and energetically optimizing the molecular structures of the at least one intermediate; (d) generating at least one quantitative structural descriptor of the geometrically and energetically optimized intermediate; (e) identifying a mathematical relationship between the at least one quantitative structural characteristic and the defined characteristic; (f) utilizing the mathematical relationship to identify at least one catalyst in a sample catalyst set having the defined characteristic; (g) contacting the identified catalyst with a reactant under conditions suitable for the production of a product; and (h) recovering the product.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

Disclosed herein are methodologies and processes for identification of catalysts having a user/process-desired characteristic. In an embodiment, the catalyst is a polymerization catalyst. In another embodiment, the catalyst is an oligomerization catalyst. Alternatively, the catalyst comprises, consists essentially of, or consists of a selective alpha-olefin polymerization catalyst. Alternatively, the catalyst comprises, consists essentially of, or consists of a selective alpha-olefin oligomerization catalyst. In some aspects, the catalyst comprises, consists essentially of, or consists of a catalyst for the production of hexene/octene or alternatively comprises, consists essentially of, or consists of a catalyst for the production of 1-hexene/1-octene.

In an embodiment, a method comprises obtaining a control catalyst set and preparing a control catalyst data set comprising one or more known characteristics of each member of the control catalyst set. Herein the known characteristics of each member of the control catalyst set are designated the control characteristics. The method may further comprise selecting at least one intermediate formed during the catalytic cycle of each member of the control catalyst set. In an embodiment of the method, the structure of the at least one intermediate identified for each member of the control catalyst set may be subjected to one or more computational methods to provide a geometrically and energetically-optimized (GEO) intermediate structure. In an embodiment, the method further comprises determining one or more characteristics of the geometrically and energetically-optimized intermediate structure. In such embodiments, the method may comprise determining a mathematical relationship between one or more characteristics of the geometrically and energetically-optimized intermediate structure and one or more control characteristics. It is to be understood that the relationship is determined between each geometrically energetically optimized intermediate and its respective member of the control catalyst set.

In an embodiment, the method further comprises identification of characteristics of the geometrically and energyoptimized intermediate and control characteristics that satisfy a mathematical condition of probabilistic dependence and expressed as a mathematical relationship. In an embodiment, the method comprises utilizing the mathematical relationship to predict the characteristics of a catalyst that is not a member of the control catalyst set. The method may further comprise contacting the catalyst that is not a member of the control catalyst set with a monomer under conditions suitable for the formation of a polymer and recovering the polymer.

An embodiment of a method disclosed herein comprises generating a predictive model from which to identify a catalyst having a desired property. The method may comprise (i) identifying a control catalyst set wherein the individual members of the control catalyst set range in one or more user and/or process desired characteristics; (ii) generating putative intermediate structures comprising the individual members of the control set associated with a reagent in the desired reaction; (iii) geometrically and energetically optimizing the molecular structures of the putative intermediate to provide a collection of structures of geometrically and energetically optimized intermediates; (iv) generating quantitative structural descriptors that characterize at least a portion of the molecular structure of the geometrically and energetically optimized intermediates; and (v) identifying a mathematical function that relates at least one quantitative structural descriptor of the geometrically and energetically optimized intermediates to the one or more user and/or process desired characteristics for the respective member of the control catalyst set. In an embodiment, the mathematical relationship may be used to identify catalysts that are not a member of the control catalyst set but have a desired property. The identified catalyst may be contacted with a monomer under conditions suitable for the formation of a polymer. The method may further comprise recovery of the polymer. Computational and comparative methods are described in more detail herein.

The term "predictive model" as defined herein refers ti a mathematical function that uses quantitative structural descriptors to calculate predicted values of the property of interest. Herein "quantitative structural descriptor" refers to a structural chemical property that has a numerical value to characterize at least a portion of the molecular structure. In an embodiment the predictive model produces calculated values which may be correlated to experimentally derived values with a correlation coefficient of from about 0.9 to about 1, alternatively from about 0.95 to about 0.99, or alternatively from about 0.980 to about 0.999.

Figure 1:
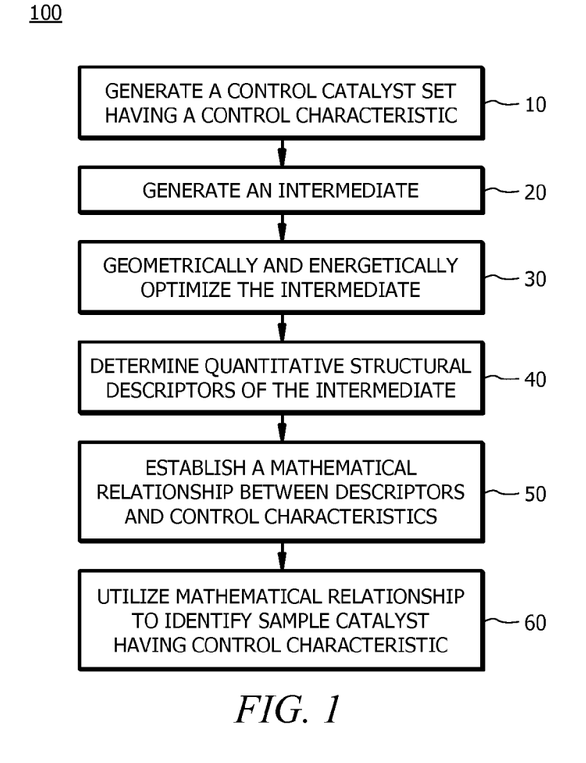
FIG. 1 depicts an embodiment of the methods disclosed herein.
Figure 2A:
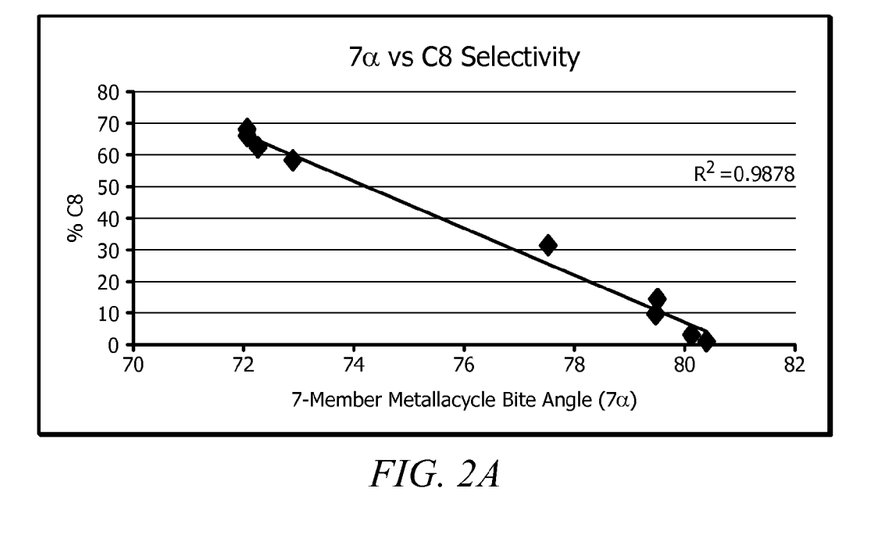
FIGS. 2A and 2B depict plots of the 1-hexene selectivity as a function of the bite angle for the 7-membered metallacycle intermediate.
Figure 2B:
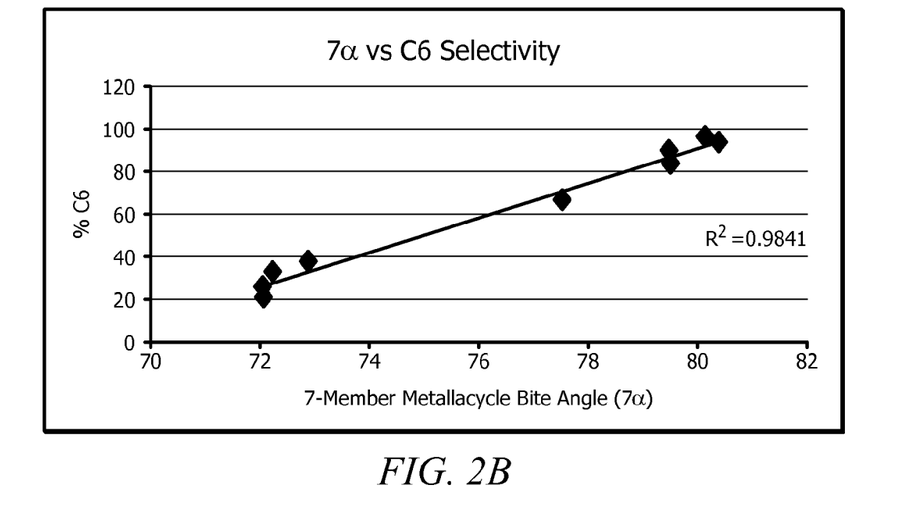
Figure 3:
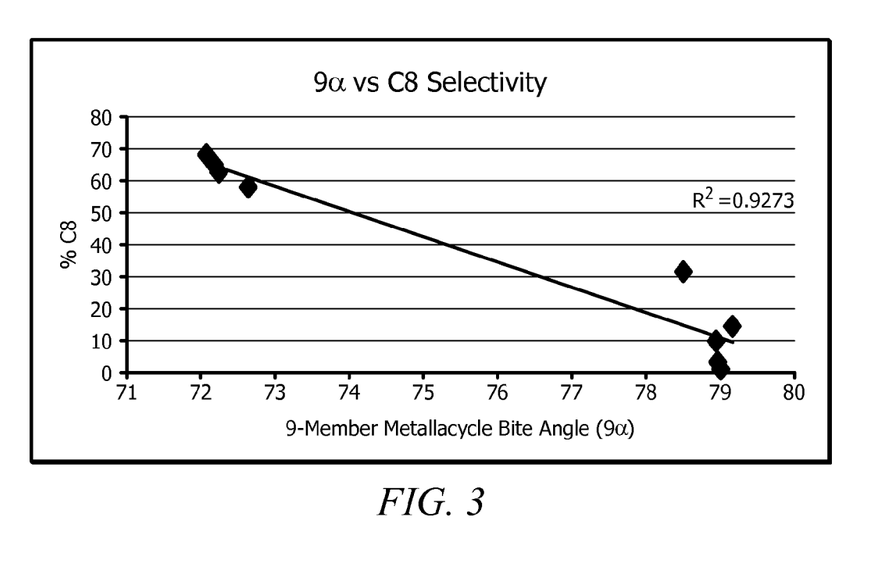
FIG. 3 depicts a plot of the 1-octene selectivity as a function of the bite angle for the 9-membered metallacycle intermediate.
Figure 4:
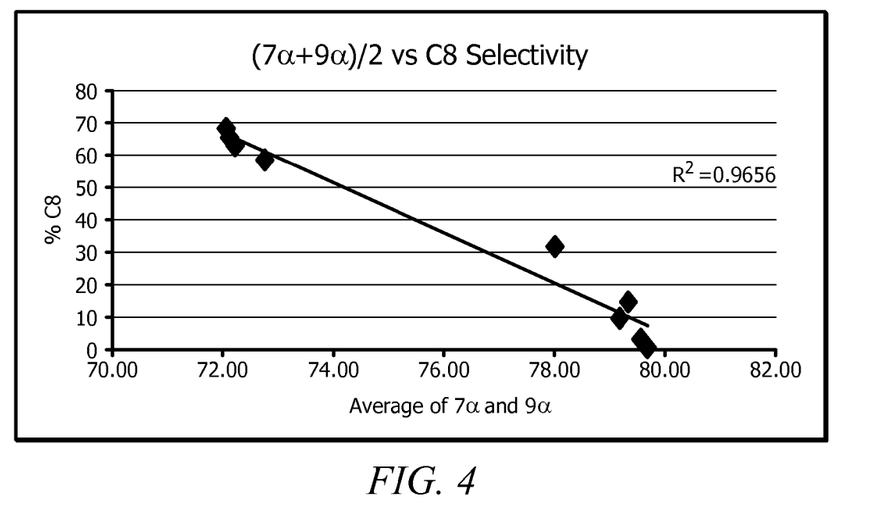
FIG. 4 depicts a plot of the 1-octene selectivity as a function of the average bite angle for the 7-membered and 9-membered metallacycle intermediate.
Figure 5:
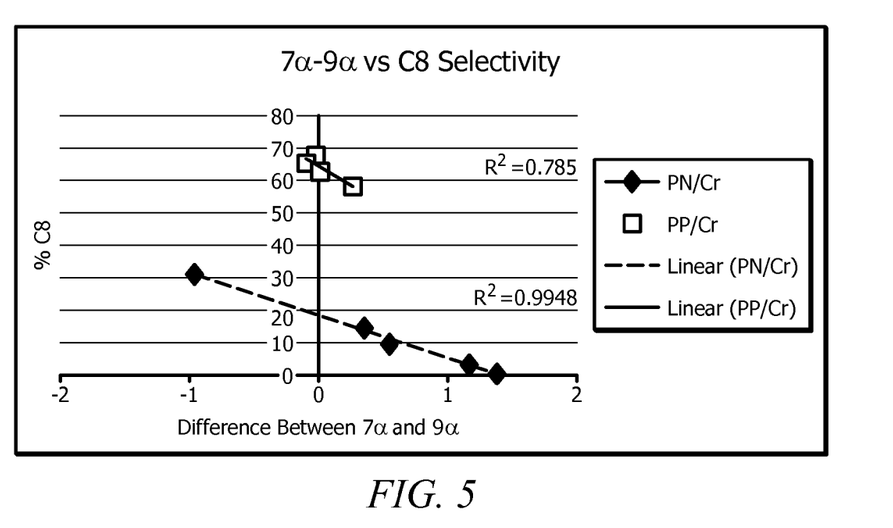
FIG. 5 depicts plots of the difference prediction for the samples of Example 1.

FIG. 1 depicts an embodiment of a method of this disclosure. Referring to FIG. 1, the method comprises generation of a control catalyst set, 10. The control catalyst set may comprise catalysts that range in value for one or more control characteristics. For example, each member of the control catalyst set may differ in terms of catalytic activity, catalyst productivity and/or catalyst selectivity. Generally catalytic productivity refers to the mass of product produced per mass of catalyst utilized; the catalyst activity refers to the mass of product produced per mass of catalyst utilized per unit time; and the catalyst selectivity is defined for each product on the basis of its formation (e.g., mass of product A, mass of product B, etc.) relative to the formation of other possible products (e.g., relative to total mass of all products).

In various embodiments herein, the disclosure may refer to utilization of a control catalyst set that comprises catalysts differing in catalyst selectivity, and it is to be understood that the methodologies disclosed herein may be utilized to analyze control catalyst sets that provide a range of values for one or more different characteristics separate or in combination with selectivity (e.g., catalytic activity, catalyst productivity, combinations thereof, etc.). The control catalyst set may contain any number of members. For example, the control catalyst set may contain from about 3 to about 100 members, alternatively from about 5 to about 20 members, or alternatively from about 5 to about 10 members. Information on the control characteristic (e.g., catalyst selectivity) for each member of the control catalyst set may be obtained experimentally, from literature sources, derived from other prior work or obtained from a combination of sources.

In an embodiment, each member of the control catalyst set is an oligomerization and/or polymerization catalyst which may be utilized in the trimerization and/or tetramerization of ethylene. In such embodiments, each member of the control catalyst set may have a catalyst selectivity that is based on the extent to which the catalyst produces the desired product, for example hexene (or 1-hexene) as opposed to octene (or 1-octene). The catalyst selectivity for 1-hexene (1-$C_6$=) of the control catalyst set as a whole may range from about 0 to about 100, alternatively from about 0 to about 50, or alternatively from about 50 to about 100. In other aspects, the catalyst selectivity for 1-octene (1-$C_8$=) of the control catalyst set as a whole may range from about 0 to about 100, alternatively from about 0 to about 50, or alternatively from about 50 to about 100. In such embodiments, the "1-$C_6$=" refers to the weight percent of ethylene converted into 1-hexene while "1-$C_8$=" refers to the weight percent of ethylene converted into 1-octene.

In an embodiment, each member of the control catalyst set is a compound comprising one or more catalytic metals (e.g., a transition metal), for example a supported catalytic metal and/or catalytic metal associated with (e.g., complexed with) a suitable ligand. A compound comprising one or more catalytic metals in an amount effective to catalyze a chemical reaction under suitable reaction conditions is referred to generally herein as a catalyst, and various embodiments herein are directed to evaluating, testing, identifying, etc. such catalysts. However, it is to be understood that in the context of a given use of such catalysts to catalyze a given reaction, such catalysts may be used individually or in various combinations, and further in combination with one or more additional compounds such as co-catalysts, activators, promoters, selectivity enhancers, and the like, and collectively such combinations may be referred to a catalyst systems. Further, it is to be understood that reference herein to a catalyst includes any such further compounds available to form a catalyst system as would typically be employed in a given reaction and as would be apparent to those skilled in the art with the aid of this disclosure.

In an embodiment, each member of the control catalyst set is a compound comprising one or more catalytic metals (e.g., a transition metal) and an organic ligand. In an embodiment, each member of the control catalyst set is a catalyst comprising a catalytic metal compound (e.g., a transition metal compound) complexed to a heteroatomic ligand. In an aspect, the heteroatomic ligand comprises a moiety characterized by having a P—N—P (phosphorus-nitrogen-phosphorus) linkage. The moiety having the P—N—P linkage may hereafter be referred to as a PNP moiety or as a diphosphino aminyl moiety. In various embodiments, such catalyst may be used for oligomerization and/or polymerization reactions (e.g., oligomerization of ethylene to 1-hexene).

In an embodiment, a member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, n ranges from about 1 to about 5, M can be a group IVB, VB, or VIB metal, X can be a halide, carboxylate, acetonate, alkoxide, phenoxide, nitrate, sulfate, phosphate, or chlorate and p is 2 or 3. In some embodiments, $R^{2c}$ is a methyl group, $R^{1c}$, $R^{3c}$, $R^{4c}$, and $R^5$ are hydrogen, and $M$-$X_p$ comprises chromium.

In other embodiments, a member of the control catalyst set may be characterized by Structure II:

Structure II wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{45}$ are each independently, hydrogen, an alkyl group, an alkoxy group, or a halogen atom, n ranges from about 1 to about 5, M can be a group IVB, VB, or VIB metal, X can be a halide, carboxylate, acetonate, alkoxide, phenoxide, nitrate, sulfate, phosphate, or chlorate and p is 2 or 3. In some embodiments, $R^{2c}$ may be a $C_1$ to $C_4$ alkyl group and $R^{1c}$, $R^{3c}$, $R^{4c}$, and $R^5$ is hydrogen, and $M$-$X_p$ comprises chromium. In some embodiments, $R^{2C}$ is a methyl group, $R^{1c}$, $R^{3c}$, $R^{4c}$, and $R^5$ are hydrogen, and $M$-$X_p$ comprises chromium.

In other embodiments, a member of the control catalyst set may be characterized by Structure III:

Structure III wherein M can be a group IVB, VB, or VIB metal, X can be a halide, carboxylate, acetonate, alkoxide, phenoxide, nitrate, sulfate, phosphate, or chlorate and p is 2 or 3. In an embodiment $M$-$X_p$ comprises chromium. Additional descriptions of metal compounds complexed to PNP ligands that are suitable for use as members of the control catalyst set can be found in U.S. Patent Publication No. 2012/0172645 which is incorporated by reference herein.

In an embodiment, a member of the control catalyst set may comprise an $N^2$-phosphinyl amidine transition metal complex characterized by Structure IV:

Structure IV wherein $R^1$ is a $C_1$ to $C_{30}$ organyl group, $R^2$ is hydrogen or a $C_1$ to $C_{30}$ organyl group consisting essentially of inert functional groups, $R^3$ is hydrogen or a $C_1$ to $C_{30}$ organyl group consisting essentially of inert functional groups, $R^4$ and $R^5$ are each independently a $C_1$ to $C_{30}$ organyl group consisting essentially of inert functional groups, M can be a group IVB, VB, or VIB metal, X can be a halide, carboxylate, acetonate, alkoxide, phenoxide, nitrate, sulfate, phosphate, or chlorate, p is 2 or 3, Q is a neutral ligand, and a ranges from 0 to 6. Additional descriptions of $N^2$-phosphinyl amidine transition metal complexes suitable for use as members of the control catalyst set can be found in WIPO Publication No. 2011/082192 which is incorporated by reference herein.

In an embodiment, a member of the control catalyst set may comprise an $N^2$-phosphinyl amidine ligand characterized by the structure: $R_2P$—X—$PR_2$, where X=—$(CH_2)_n$—, —$(CHR)_n$—, NH—$(CHR)_n$—NH, O—$(CHR)_n$—O, o-$C_6H_4$, —CH=CH—.

In an embodiment, a member of the control catalyst set comprises a ligand of the general formula $R^1R^2P$—($NR^3$)—$PR^4$—($NR^5H$) where $R^1$, $R^2$, $R^3$, $R^4$ and $R^5$ are independently selected from $C_1$-$C_{14}$-alkyl, aryl and substituted aryl, wherein the PNPN-ligand chelates the metal center in a bidentate fashion via P,N or P,P-coordination.

Referring to FIG. 1, the method further comprises selecting at least one commonly known and/or putative intermediate in the catalytic cycle for each member of the control catalyst set, 20. Herein the "catalytic cycle" refers to the multistep reaction mechanism that leads to the formation of products from reactants. As will be understood by one of ordinary skill in the art, the "commonality" of the known or putative intermediate is to be considered in view of the features known or purported to influence the catalytic cycle. Thus, the commonly known or putative intermediate(s) will share features that influence the catalytic cycle but are not necessarily structurally identical compounds.

Also as will be understood by one of ordinary skill in the art, during the catalytic cycle any number of intermediates may form preceding formation of the product. Further, the temporal stability of any particular intermediate in the catalytic cycle may be such that the intermediate structure is not identifiable using typical analytical methodologies. In such embodiments, the intermediate structure in terms of the constituent atoms and their arrangement is putative and may be speculated based on scientific principles. In other embodiments, the intermediate is temporally stable and may be characterized by suitable analytical methodologies.

In an embodiment, at least one commonly known and/or putative intermediate is chosen based on the known or postulated influence of the intermediate on formation of the product or progression of the catalytic cycle. For example, the intermediate chosen may be known or postulated to be involved in a rate-determining step of the reaction. In some embodiments, the method comprises selecting a plurality of commonly known and/or putative intermediates in the catalytic cycle and generating a molecular model of the commonly known and/or putative intermediates.

Herein the molecular model of the commonly known and/or putative intermediate refers to a computational rendering of the structure of the commonly known and/or putative intermediate. Such computational renderings may be constructed utilizing any suitable software (e.g., molecular modeling software). Non-limiting examples of programs which may be used to construct the molecular model are SYBYL, CERIUS2, ADAPT, SPARTAN, GAUSSIAN, JAGUAR, AMSTERDAM DENSITY FUNCTIONAL program package, GAMESS, and Q-CHEM. In an embodiment, the molecular model of the commonly known and/or putative intermediate as initially generated represents a conformer of the compound that is neither geometrically nor energetically optimized. Herein "geometrically optimized" refers to the molecular geometry which minimizes the strain on a given system (e.g., molecular model) such that any perturbation from this geometry will induce the system to change so as to reduce this perturbation unless prevented by external forces. Herein "energetically optimized" refers to the configuration of atoms wherein the temperature of the system is approximately zero. In some embodiments, the molecular geometry which minimizes strain on the system and the configuration of atoms wherein the temperature of the system is approximately zero are the same. In some embodiments, the commonly known or putative intermediate as initially generated represents a conformer of the compound that is geometrically optimized but not energetically optimized. Alternatively, the commonly known or putative intermediate as initially generated represents a conformer of the compound that is energetically optimized but not geometrically optimized.

Referring to FIG. 1, the method further comprises subjecting the molecular model to computational geometric and/or energetic optimization, 30. The computational geometric and/or energetic optimization may be carried out using any suitable software package, such as those disclosed herein. In an embodiment, the molecular model is subjected to a molecular dynamic simulation such as conformational searching and at least one geometrically and energetically optimized (GEO) intermediate is identified for each control catalyst.

Referring to FIG. 1, the method further comprises determining a plurality of quantitative structural descriptors of the GEO intermediate comprising information on at least a portion of the molecular structure of the compound, 40. Nonlimiting examples of quantitative structural descriptors of the GEO intermediate include the expected positions of the constitutive atoms, the absolute and relative energies, electronic charge distributions, dipoles and higher multipole moments, vibrational frequencies, individual bond lengths, bond angles, dihedral angles, and combinations thereof. Any suitable methodology may be employed for determining quantitative structural descriptors of the GEO intermediate. For example, quantitative structural descriptors may be obtained from databases and/or computed directly from the molecular model of the GEO intermediate.

Referring to FIG. 1, the method further comprises identification of a mathematical relationship (e.g. in the form of a mathematical function or equation) that relates one or more quantitative structural descriptors of each GEO intermediate to the catalyst selectivity of the respective member of the control catalyst set, 50. In an embodiment, any suitable methodology may be utilized for identification of a mathematical relationship that relates one or more quantitative structural descriptors of each GEO intermediate to the catalyst selectivity of the respective member of the control catalyst set.

For example, a quantitative structural descriptor for each GEO intermediate may be plotted as a function of the catalyst selectivity for each respective member of the control catalyst set. The plot may then be analyzed using conventional statistical methodologies to identify the existence of a relationship between the plotted variables. In an embodiment, the analysis is univariate and takes into consideration a single quantitative descriptor for each GEO intermediate and its relationship to the catalyst selectivity of the respective member of the control catalyst set.

Alternatively, the analysis is multivariate and takes into consideration a plurality of quantitative structural descriptors for each GEO intermediate and its relationship to the catalyst selectivity of the respective member of the control catalyst set. In such embodiments, a mathematical relationship is identified between at least two quantitative structural descriptors for the GEO intermediate and the catalyst selectivity of the respective member of the control catalyst set.

Any suitable methodology for multivariate analysis may be employed. For example, multivariate analysis of the quantitative structural descriptors of the GEO intermediate in relation to the catalyst selectivity may be carried out using any suitable chemometric technique. Examples of suitable chemometric techniques include but are not limited to Partial Least Squares Regression (PLS), Multilinear Regression Analysis (MLR), Principal Components Regression (PCR), Principal Component Analysis (PCA) and Discriminant Analysis, as well as Design of Experiment (DOE) and Response Surface Methodologies. In an embodiment, the chemometric analysis is carried out using PLS, which refers to a wide class of methods for modeling relations between sets of observed variables by means of latent variables. The underlying assumption of all PLS methods is that the observed data is generated by a system or process which is driven by a small number of latent variables.

In an embodiment, utilizing either univariate or multivariate analysis as described herein, a mathematical relationship between at least one quantitative structural descriptor of the GEO intermediate and the catalyst selectivity of the respective member of the control catalyst set is identified.

In an embodiment, a linear mathematical relationship between at least one quantitative structural descriptor of the GEO intermediate and the catalyst selectivity of the respective member of the control catalyst set is identified. Alternatively, the mathematical relationship identified is nonlinear. The relationship between the quantitative structural descriptor of the GEO intermediate and the catalyst selectivity of the respective member of the control catalyst set may satisfy the statistical condition of probabilistic dependence.

In an embodiment the relationship between the quantitative structural descriptor of the GEO intermediate and the catalyst selectivity of the respective member of the control catalyst set is linear and when subjected to regression analysis provides a coefficient of determination ($R^2$) ranging from about 0.9 to about 1.0, alternatively from about 0.95 to about 0.99, or alternatively from about 0.980 to about 0.999. Herein a quantitative structural descriptor of the GEO intermediate that is identified to have a mathematical relationship (e.g., linear relationship) to the catalyst selectivity of the respective member of the control catalyst set is termed a predictive descriptor.

Referring to FIG. 1, the method further comprises, at 60, utilizing the mathematical relationship employing the predictive descriptor as a predictive model to predict catalyst selectivity for a catalyst that is not a member of the control catalyst set, herein designated the sample catalyst. It is to be understood that the mathematical relationship established between the GEO intermediate predictive descriptor and the catalyst selectivity of the respective member of the control catalyst set may be utilized to predict the catalyst selectivity of structurally similar sample catalysts. A marked divergence of the catalyst structure of the sample catalyst from that of the catalysts in the control catalyst set may strain the mathematical relationship identified to exist between the predictive descriptor and catalyst selectivity to the extent that is no longer predictive of the catalyst selectivity. For example, when considering catalyst structures of the type exemplified herein (e.g., Structures I, II, III, and IV) it is expected to for catalysts forming similar intermediates (e.g., five, seven, or nine-membered metallacycles) the relationship will remain robust.

In an embodiment, the sample catalyst comprises a catalytic metal (e.g., a transition metal) and organic ligand of the type present in the members of the control catalyst set. In an embodiment, the sample catalyst is experimentally obtained through suitable synthetic methodologies. In the alternative, the sample catalyst is a theoretical compound that has not been synthesized.

In an embodiment, the mathematical relationship established between the GEO intermediate predictive descriptor and the catalyst selectivity of the respective member of the control catalyst set is utilized to predict the catalyst selectivity of a structurally similar sample catalyst by (i) generating a GEO intermediate for the sample catalyst and determining the value of the predictive descriptor for the sample catalyst, and (ii) utilizing the predictive descriptor of the sample catalyst in the mathematical relationship derived from the control catalyst set to predict the catalyst selectivity of the sample catalyst.

In an embodiment, the mathematical relationship established between the GEO intermediate predictive descriptor and the catalyst selectivity of the respective member of the control catalyst set is utilized to predict the catalyst selectivity of structurally similar sample catalysts by the following predictive method. In an embodiment, the predictive method comprises a obtaining a sample catalyst set. The sample catalyst set may contain any number of members. For example the sample catalyst set may contain from about 3 to about 100 members, alternatively from about 5 to about 20 members, or alternatively from about 5 to about 10 members. In some embodiments, the sample catalyst set comprises hypothetical catalysts wherein the sample catalyst has not been synthesized. Each member of the sample catalyst set may be characterized as having unknown catalyst selectivity and structural similarity to at least one member of the control catalyst set. In an embodiment, the predictive method may comprise generating at least one GEO intermediate for each member of the sample catalyst set and determining the value of the predictive descriptor for each GEO intermediate. The predictive descriptor of the GEO intermediate may be used to predict the catalyst selectivity for the respective sample catalyst, for example by utilizing the predictive descriptor of the sample catalyst in the mathematical relationship derived from the control catalyst set to predict the catalyst selectivity of the sample catalyst (e.g., via plugging a predictive descriptor value into a liner relationship that may be defined graphically and/or via an equation such as a curve fit equation to yield a corresponding value for a desired catalytic characteristic such as selectivity). Thus, it is contemplated that the methodologies disclosed herein may be employed in the screening of any number of actual or hypothetical sample catalysts for a desired characteristic (e.g., catalyst selectivity). In an embodiment, a sample catalyst predicted to have desired catalyst selectivity is chosen from a plurality of catalysts and designated herein the catalyst having identified catalyst selectivity (CHICS), and in some embodiments such CHICS may be subjected to further evaluation via testing such as catalytic reaction testing and evaluation of resultant catalytic characteristics such as selectivity under various reaction conditions to identify candidates for use in commercial-scale catalytic reactions and processes.

In some embodiments, the CHICS may be subjected to one or more methodologies to experimentally determine the value of the desired characteristic. In such embodiments, the experimentally determined value may be compared to the value derived utilizing the mathematical relationship. As will be understood by one of ordinary skill in the art, such comparisons may provide a metric with which to evaluate the robustness of the mathematical relationship established between the GEO intermediate predictive descriptor and the catalyst selectivity of the respective member of the control catalyst set.

In an embodiment, CHICS as described herein may be employed in the polymerization and/or oligomerization of olefins. Such a process may be carried out by contacting a catalyst system comprising one or more CHICS and an optional cocatalyst with one or more olefin monomers under reaction conditions suitable for polymerization or oligomerization of olefins. In some embodiments, the polymerization or oligomerization process comprises 1) contacting an olefin, a CHICS, and a cocatalyst; and 2) forming an olefin polymer or oligomer. In other embodiments, the polymerization or oligomerization process is an alpha olefin production process comprising: 1) contacting ethylene, a CHICS, and a cocatalyst; and 2) forming a product stream comprising alpha olefins. In other embodiments, the polymerization or oligomerization process is an alpha olefin production process comprising: 1) contacting ethylene, a CHICS, and a cocatalyst; and 2) forming a product stream comprising hexene and/or octene. The process may comprise additional steps such as deactivating the catalyst and/or isolating the olefin oligomer or polymer. Suitable monomers for the olefin polymerization or oligomerization may be olefins having 2 to 20 carbon atoms; alternatively, olefins having 2 to 3 carbon atoms; alternatively, ethylene.

Generally, the cocatalyst may be any organometallic compound capable of activating the CHICS to polymerize or oligomerize olefins. Suitable cocatalysts may include monomeric or oligomeric metal alkyls, metal aryls, metal alkylaryls comprising at least one of the metals selected from the group consisting of B, Al, Be, Mg, Ca, Sr, Ba, Li, Na, K, Rb, Cs, Zn, Cd, and Sn. In some embodiments, the cocatalyst may be an organoaluminum compound. Applicable organoaluminum compounds may include trialkylaluminums, alkylaluminum halides, alumoxanes or mixture thereof. In some embodiments, the organoaluminum compound may be trimethylaluminum triethylaluminum, diethylaluminum chloride, diethylaluminum ethoxide, diethylaluminum cyanide, diisobutylaluminum chloride, triisobutylaluminum, ethylaluminum sesquichloride, methylalumoxane (MAO), modified methylalumoxane (MMAO), isobutyl alumoxanes, t-butyl alumoxanes, or mixtures thereof. In other embodiments, the organoaluminum compounds may include methylalumoxane (MAO), modified methylalumoxane (MMAO), isobutyl alumoxanes, t-butyl alumoxanes, or mixtures thereof. In other embodiments, the cocatalyst may be methylalumoxane, modified methylalumoxane, or mixtures thereof. In yet other embodiments, the cocatalyst may be methylalumoxane; alternatively, modified methylalumoxane; isobutylalumoxane (IBAO); or alternatively, partially hydrolyzed trialkylaluminum.

In embodiments, the polymerization or oligomerization reaction may occur in a solvent or diluent. In some embodiments, the solvent or diluent may comprise a $C_4$ to $C_{20}$ hydrocarbon; or alternatively, a $C_4$ to $C_{10}$ hydrocarbon. The hydrocarbon solvent may be a saturated hydrocarbon, an aromatic hydrocarbon or an olefinic hydrocarbon. In some embodiments, the saturated hydrocarbon solvent may be a $C_4$ to $C_{10}$ saturated hydrocarbon. In other embodiments, the saturated solvent may be butane, isobutane, hexane, heptane, cyclohexane, or mixtures thereof. In some embodiments, the aromatic solvent may be a $C_6$ to $C_{20}$ aromatic compound. In some embodiments, the aromatic solvent may be benzene, toluene, xylene(s), ethylbenzene, or mixtures thereof. In other embodiments, another embodiment, the olefinic hydrocarbon solvent may comprise alpha olefins. In other embodiments, the alpha olefin solvent comprises a $C_4$ to $C_{20}$ alpha olefin; alternatively, a $C_4$ to $C_{12}$ alpha olefin; alternatively, alternatively, a $C_{12}$ to $C_{18}$ alpha olefin. In yet other embodiments, the alpha olefin solvent may be 1-butene, 1-dodecene, 1-tetradecene, 1-hexadecene, 1-octadecene, or combinations thereof.

Unless specified otherwise, the terms contacted, combined, and "in the presence of" refer to any addition sequence, order, or concentration for contacting or combining two or more components of the polymerization reaction. Combining or contacting of polymerization or oligomerization components, according to the various methods described herein may occur in one or more contact zones under suitable contact conditions such as temperature, pressure, contact time, flow rates, etc. . . . The contact zone may be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. The methods may be carried out in a batch or continuous process as is suitable for a given embodiment, with physical parameters of the contact zone being specified accordingly.

In embodiments, the polymerization or oligomerization may be a continuous process carried out in one or more reactors. In some embodiments, the continuous polymerization or oligomerization process reactor may comprise a loop reactor, a tubular reactor, a continuous stirred tank reactor (CSTR), or combinations thereof. In other embodiments, the continuous polymerization or oligomerization process reactor may be a loop reactor; alternatively, a tubular reactor; or alternatively, a continuous stirred tank reactor (CSTR). In other embodiments, the continuous polymerization or oligomerization process reactor may be employed in the form of different types of continuous reactors in combination, and in various arrangements. In an embodiment, the continuous reactor may be a combination of a tubular reactor and a CSTR. In other embodiments, the continuous polymerization or oligomerization process reactor may be two or more reactors in series, two or more reactors in parallel, or combinations thereof. In an embodiment, the continuous polymerization or oligomerization process reactor may be more than one CSTR in series. In another embodiment, the continuous reactor may be a tubular reactor and a loop reactor in series. In yet another embodiment, the continuous reactor may be two or more loop reactors in series.

Suitable polymerization or oligomerization reaction conditions such as temperatures, pressures and times may be impacted by a number of factors such as the identity of the CHICS, stability of the CHICS, cocatalyst identity, cocatalyst activity, desired product desired product distribution, and/or desired product purity among others. Such factors may be adjusted using any suitable methodology in order to achieve the desired objectives.

The reaction temperature of the polymerization or oligomerization reaction may be any reaction temperature required to produce the desired polymerization or oligomerization product. In some embodiments, the reaction temperature for the polymerization or oligomerization reaction may range from –20° C. to 200° C. In some embodiments, the polymerization or oligomerization temperature ranges from 0° C. to 150° C.; alternatively, ranges from 10° C. to 150° C.; alternatively, ranges from 20° C. to 100° C.; or alternatively, ranges from 30° C. to 80° C.

The reaction pressure of the polymerization or oligomerization reaction may be any reaction pressure required to produce the desired polymerization or oligomerization product. In some embodiments, the polymerization or oligomerization reaction pressure may be greater than 0 psig (0 KPa); alternatively, greater than 50 psig (344 KPa); alternatively, greater than 100 psig (689 KPa); or alternatively, greater than 150 psig (1.0 MPa). In other embodiments, the polymerization or oligomerization reaction pressure may range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the monomer is a gas (e.g. ethylene), the polymerization or oligomerization reaction may be carried out under a monomer gas pressure. When the polymerization or oligomerization reaction produces ethylene oligomerization products, the reaction pressure may be the monomer ethylene pressure. In some embodiments, the ethylene pressure may be greater than 0 psig (0 KPa); alternatively, greater than 50 psig (344 KPa); alternatively, greater than 100 psig (689 KPa); or alternatively, greater than 150 psig (1.0 MPa). In other embodiments, the ethylene pressure may range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases when ethylene is the monomer, inert gases may form a portion of the total reaction pressure. In the cases where inert gases form a portion of the reaction pressure, the previously stated ethylene pressures may be the applicable ethylene partial pressures of the polymerization or oligomerization reaction. In the situation where the monomer provides all or a portion of the polymerization or oligomerization reaction pressure, the reaction system pressure may decrease as the gaseous monomer is consumed. In this situation, additional gaseous monomer and/or inert gas may be added to maintain a desired polymerization or oligomerization reaction pressure. In embodiments, additional gaseous monomer may be added to the polymerization or oligomerization reaction at a set rate (e.g. for a continuous flow reactor), at different rates (e.g. to maintain a set system pressure in a batch reactor). In other embodiments, the polymerization or oligomerization reaction pressure may be allowed to decrease without adding any additional gaseous monomer and/or inert gas.

The reaction time of the polymerization or oligomerization reaction may be any reaction time required to produce the desired quantity of polymerization or oligomerization product, obtain a desired catalyst productivity, and/or obtain a desired conversion of monomer. In some embodiments, the polymerization or oligomerization reaction time ranges from 1 minute to 5 hours; alternatively, ranges from 5 minutes to 2.5 hours; alternatively, ranges from 10 minutes to 2 hours; or alternatively, ranges from 1 minute to 1.5 hours.

In an aspect, the oligomerization process utilizing the CHICS may produce alpha olefins. In some embodiments, the product comprises linear alpha olefins having at least 4 carbon atoms. Generally, the oligomerization process producing alpha olefins having at least four carbon atoms produces a distribution of several alpha olefins that may be described by a Schulz-Flory chain growth factor K, where K is defined by the equation:

$$K = X_{q+2}/X_n$$

wherein $X_{q+2}$ is the number of moles of alpha olefin produced having q+2 carbon atoms and $X_n$ is the number of moles of alpha olefin produced having n carbon atoms (i.e. the moles of the preceding alpha olefin produced). In some embodiments, the alpha olefin product distribution may be described as having a Schulz-Flory chain growth factor K of from about 0.4 to about 0.8, alternatively from about 0.45 to about 0.65, or alternatively from about 0.55 to about 0.65. Generally, the Schulz-Flory growth factor may be measured using the number of moles alpha olefins of any two adjacent produced alpha olefins. The measured Schulz-Flory growth factor may not be exactly the same using the number of moles of alpha olefin produced for every possible adjacent pair of produced alpha olefins. Thus, in some embodiments, the Schulz-Flory growth factor may be an average of two or more adjacent pairs of produced alpha olefins.

In another aspect, the oligomerization process may produce an alpha olefin product with high selectivity to linear alpha olefins. In some embodiments, the oligomerization process produces a reactor effluent wherein the oligomerized product having 6 carbon atoms has a 1-hexene content of from about 80% to about 100%, alternatively from about 90% to about 100%, or alternatively from about 98% to about 100%. In other embodiments, the oligomerization process produces a reactor effluent wherein the oligomerized product having 8 carbon atoms has a 1-octene content of from about 90% to about 100%, alternatively from about 98% to about 100%, or alternatively from about 99% to about 100%. In yet other embodiments, the oligomerization process produces a reactor effluent wherein the oligomerized product having 10 carbon atoms has a 1-decene content of from about 0% to about 20%, alternatively from about 0% to about 10%, or alternatively from about 5% to about 10%. In yet other embodiments, the oligomerization process produces a reactor effluent wherein the oligomerized product having 6 carbon atoms comprises any weight percent 1-hexene as described herein, the oligomerized product having 8 carbon atoms comprises any weight percent 1-octene as described herein, and the oligomerized product having 10 carbon atoms comprises any weight percent 1-decene as described herein.

In an embodiment, the methods disclosed herein are utilized to identify sample catalysts having a user and/or process desired catalyst selectivity based on the production of 1-hexene compared to 1-octene during an ethylene polymerization reaction. In an embodiment, the control catalyst set comprises members having P—N—P ligands which function as catalysts for the polymerization and/or oligomerization of ethylene to produce 1-hexene and/or 1-octene. For example each member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, n ranges from about 1 to about 5, M can be a group IVB, VB, or VIB metal, X can be a halide, carboxylate, acetonate, alkoxide, phenoxide, nitrate, sulfate, phosphate, or chlorate and p is 2 or 3. In some embodiments, $R^{2c}$ is a methyl group, $R^{1c}$, $R^{3c}$, $R^{4c}$, and $R^5$ are hydrogen, and $M-X_p$ comprises chromium. In such embodiments, a putative reaction mechanism for the catalytic cycle of the members of the control catalyst set may be as depicted in Scheme I:

Scheme I

Referring to Scheme I, the proposed catalytic cycle consists of two possible pathways for product formation. One pathway involves a possible agostic interaction between the proton in the β position to the transition metal, resulting in β-hydride elimination yielding either the η2-coordinated hexene on the transition metal and a seven(7)-membered metallacycle or the η2 coordinated octene on the transition metal and a nine(9)-membered metallacycle. In an embodiment, at least two GEO intermediates are prepared. A first GEO intermediate is prepared from a molecular model of the 7-membered metallacycle while a second GEO intermediate is prepared from a molecular model of the 9-membered metallacycle.

In an embodiment the predictive descriptor is utilized to identify sample catalysts having some user and/or process desired product selectivity for the production of 1-hexene and/or 1-octene from ethylene. In such embodiments, the predictive descriptor is the phosphorus-nitrogen-phosphorus (PNP) bite angle identified in Table 2. In such embodiments the mathematical relationship between the PNP bite angle is such that increases in the bite angle favor formation of 1-hexene while decreases in the bite angle favor formation of 1-octene. For example for bite angles of PNP catalysts of the type characterized by Structure A-D ranging from about 68 degrees to about 74 degrees, alternatively from about 71 degrees to about 74 degrees or alternatively from about 72 degrees to about 73 degrees, the 1-hexene:1-octene product ratio ranges from about 0.1 to about 1, alternatively from about 0.2 to about 0.8 or alternatively from about 0.3 to about 0.6. For example for bite angles of PN catalysts of the type characterized by Structure 1-5 ranging from about 74 degrees to about 84 degrees, alternatively from about 76 degrees to about 82 degrees or alternatively from about 77.5 degrees to about 80.5 degrees the 1-hexene:1-octene product ratio ranges from about 0.2 to about 200, alternatively from about 0 to about 150 or alternatively from about 1 to about 100.

EXAMPLES

The data and descriptions provided in the following examples are given to show particular embodiments of the catalysts and methods disclosed, and to demonstrate a number of the practices and advantages thereof. The examples are given as a more detailed demonstration of some of the embodiments described above, and are not intended to limit the specification or the claims to follow in any manner.

The methodologies disclosed herein were investigated. Table 1 provides the structures of the PNP ligands A-D and PN—Cr complexes Structures 1-6 that were evaluated using the disclosed methodologies.

TABLE 1

The GEO intermediates utilized for each complex were the 7-member metallacycle and the 9-membered metallacycle depicted in Table 2. The GEO intermediates for each PNP—Cr or PN—Cr complex were determined by molecular modeling of the cationic Cr(III) metallacyle using density functional theory with the following method: (i) all optimizations assumed Cr(III) cation with quartet spin state; (ii) the initial geometries were obtained via PM3 geometry optimizations with conformational searching in the software package SPARTAN 08; and (iii) PM3 structures were refined in SPARTAN 08 using DFT B3LYP with the LACVP basis set having the LANL2DZ effective core potential on Cr and P and 6-31G on H, C, and N. PM3 geometry optimizations refer to semi-empirical methods, while the basis set refers to the linear combinations of atomic orbitals that is used as a mathematical description of the orbitals of a system. The P—Cr—N and P—Cr—P bite angles were found to correlate to the catalyst selectivity for the control catalyst set. The ability of the P—Cr—N and P—Cr—P bite angles to predict the catalyst selectivity of sample catalysts was investigated. The bite angles are contained in the data set for the GEO intermediates using the angle measurement tool in SPARTAN. Those calculated bite angles (N—Cr—P and P—Cr—P) were then compared to experimentally determined C8 and C6 selectivities in oligomerizations conducted under similar catalytic conditions.

TABLE 2 bite angle 7-member metallacycle 9-member metallacycle

PNP—Cr and PN—Cr complexes were prepared by reacting the precatalysts [L-CrCl$_3$(THF)$_n$]$_m$ (where n=0, 1, or 2; m=1 or and L=the PNP or PN ligand) with MMAO-3A (Al/Cr=400-1000) for at least 30 minutes and reacted with ethylene (900 psig) in the presence of hydrogen (25 psig) and cyclohexane at 70 C for 30 minutes. The C6 and C8 selectivity (wt. %) was determined by GC-FID and only represents selectivity in the liquid phase. The bite angle was plotted as a function of the product selectivity as indicated in FIGS. 2-5. The results summarized in Table 3 demonstrate a robust correlation between the bite angle and the C6 and C8 selectivity.

The following are enumerated embodiments which are provided as non-limiting examples:

A first embodiment which is a method comprising obtaining a control catalyst set having a plurality of members each having a control characteristic, wherein the members of the control catalyst set comprise a transition metal and an organic ligand; selecting an intermediate formed during a catalytic cycle of each member of the control catalyst set; geometrically and energetically optimizing a structure of the intermediate; determining one or more characteristics of the geometrically and energetically optimized structure of the intermediate; determining a mathematical relationship between the control characteristic and the one or more characteristics of the geometrically and energetically optimized structure of the intermediate; utilizing the mathematical relationship to identify one or more members of a sample catalyst set having a control characteristic within a desired range; contacting the identified sample catalyst with a reactant under conditions suitable for the formation of product; and recovering the product.

A second embodiment which is the method of the first embodiment wherein the transition metal comprises chromium.

A third embodiment which is the method of any of the first through second embodiments wherein the catalytic cycle comprises an oligomerization and/or polymerization reaction.

A fourth embodiment which is the method of any of the first through third embodiments wherein a member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group; $R^{1c}$, $R^{2c}$, $R^{3c}$, $R^{4c}$, and $R^{5c}$ are each independently hydrogen or an alkyl group; n ranges from about 1 to about 5; M is a group IVB, VB, or VIB metal; X is a halide, carboxylate, acetonate, alkoxide, phenoxide, nitrate, sulfate, phosphate, or chlorate; and p is 2 or 3.

A fifth embodiment which is the method of any of the first through fourth embodiments wherein a member of the control catalyst set may be characterized by Structure II:

Structure II wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are each independently, hydrogen, an alkyl group, an alkoxy group, or a halogen atom, n ranges from about 1 to about 5; M is a group IVB, VB, or VIB metal; X is a halide, carboxylate, acetonate, alkoxide, phenoxide, nitrate, sulfate, phosphate, or chlorate; and p is 2 or 3.

A sixth embodiment which is the method of any of the first through fifth embodiments wherein a member of the control catalyst set may be characterized by Structure IV:

Structure IV wherein $R^1$ is a $C_1$ to $C_{30}$ organyl group; $R^2$ is hydrogen or a $C_1$ to $C_{30}$ organyl group consisting essentially of inert functional groups; $R^3$ is hydrogen or a $C_1$ to $C_{30}$ organyl group consisting essentially of inert functional groups; $R^4$ and $R^5$ are each independently a $C_1$ to $C_{30}$ organyl group consisting essentially of inert functional groups; M is a group IVB, VB, or VIB metal; X is a halide, carboxylate, acetonate, alkoxide, phenoxide, nitrate, sulfate, phosphate, or chlorate; p is 2 or 3; Q is a neutral ligand; and a ranges from 0 to 6.

A seventh embodiment which is the method of any of the first through sixth embodiments wherein the one or more characteristics of the geometrically and energetically optimized structure of the intermediate comprise expected positions of the constitutive atoms, the absolute and relative energies, electronic charge distributions, dipoles and higher multipole moments, vibrational frequencies, individual bond lengths, bond angles, dihedral angles, or combinations thereof.

An eighth embodiment which is the method of any of the first through seventh embodiments wherein the control characteristic comprises catalytic activity, catalyst productivity, catalyst selectivity, or combinations thereof.

A ninth embodiment which is the method of any of the first through eighth embodiments wherein the mathematical relationship is a linear relationship.

A tenth embodiment which is the method of any of the first through eighth embodiments wherein the mathematical relationship is a non-linear relationship.

An eleventh embodiment which is the method of any the first through tenth embodiments wherein the reactant comprises ethylene.

A twelfth embodiment which is the method of any of the first through eleventh embodiments wherein the product comprises a mixture of 1-hexene and 1-octene.

A thirteenth embodiment which is a product produced according to the method of embodiment 1 having a desired ratio of 1-hexene:1-octene.

A fourteenth embodiment which is a method of generating a predictive model comprising (a) identifying a control catalyst set wherein individual members of the control catalyst set range in a defined characteristic; (b) preparing molecular structures of at least one intermediate in a catalytic cycle of each member of the control catalyst set; (c) geometrically and energetically optimizing the molecular structures of the at least one intermediate; (d) generating at least one quantitative structural descriptor of the geometrically and energetically optimized intermediate; (e) identifying a mathematical relationship between the at least one quantitative structural characteristic and the defined characteristic; (f) utilizing the mathematical relationship to identify at least one catalyst in a sample catalyst set having the defined characteristic; (g) contacting the identified catalyst with a reactant under conditions suitable for the production of a product; and (h) recovering the product.

A fifteenth embodiment which is the method of the fourteenth embodiment wherein the control catalyst set comprises from about 3 to about 100 members and the sample catalyst set comprises from about 3 to about 100 members.

A sixteenth embodiment which the method of any of the fourteenth through fifteenth embodiments wherein the reactant comprises ethylene.

A seventeenth embodiment which is the method of any of the fourteenth through sixteenth embodiments wherein the product comprises a mixture of 1-hexene and 1-octene.

An eighteenth embodiment which is the method of any of the fourteenth through seventeenth embodiments wherein the quantitative structural descriptor comprises expected positions of the constitutive atoms, the absolute and relative energies, electronic charge distributions, dipoles and higher multipole moments, vibrational frequencies, individual bond lengths, bond angles, dihedral angles, or combinations thereof.

A nineteenth embodiment which is the method of any of the fourteenth through eighteenth embodiments wherein a member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group; $R^{1c}$, $R^{2c}$, $R^{3c}$, $R^{4c}$, and $R^{5c}$ are each independently hydrogen or an alkyl group; n ranges from about 1 to about 5; M is a group IVB, VB, or VIB metal; X is a halide, carboxylate, acetonate, alkoxide, phenoxide, nitrate, sulfate, phosphate, or chlorate; and p is 2 or 3.

A twentieth embodiment which is the method of any of the fourteenth through nineteenth embodiments wherein the geometrically energetically optimized intermediate comprises a 7-membered metallacyle, a 9-membered metallacycle or both.

What is claimed is:
1. A method comprising:
obtaining a control catalyst set having a plurality of members each having a control characteristic, wherein the control characteristic comprises catalytic activity, catalyst productivity, catalyst selectivity, or combinations thereof, wherein the members of the control catalyst set comprise a transition metal and an organic ligand, wherein the organic ligand comprises a diphosphino aminyl moiety or an $N^2$-phosphinyl amidine moiety;
selecting an intermediate formed during a catalytic cycle of each member of the control catalyst set;
geometrically and energetically optimizing a structure of the intermediate, wherein the geometrically and energetically optimized intermediate comprises a 5-membered metallacycle, a 7-membered metallacycle, or a 9-membered metallacycle;

determining one or more characteristics of the geometrically and energetically optimized structure of the intermediate, wherein the one or more characteristics comprise a phosphorus-nitrogen-phosphorus (PNP) bite angle or a phosphorus-nitrogen (PN) bite angle;

determining a mathematical relationship between the control characteristic and the one or more characteristics of the geometrically and energetically optimized structure of the intermediate;

utilizing the mathematical relationship to identify one or more members of a sample catalyst set having the control characteristic within a desired range, wherein the one or more members of the sample catalyst set forms an intermediate comprising a 5-membered metallacycle, a 7-membered metallacycle, or a 9-membered metallacycle during a catalytic cycle;

contacting the identified sample catalyst with ethylene under conditions suitable for the formation of a mixture of 1-hexene and 1-octene; and recovering the mixture of 1-hexene and 1-octene.

2. The method of claim 1 wherein the transition metal comprises chromium.

3. The method of claim 1 wherein the catalytic cycle comprises an oligomerization and/or polymerization reaction.

4. The method of claim 1 wherein a member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group;

$R^{1c}$, $R^{2c}$, $R^{3c}$, $R^{4c}$, and $R^{5c}$ are each independently hydrogen or an alkyl group;

n ranges from about 1 to about 5;

M is a group IVB, VB, or VIB metal;

X is a halide, carboxylate, acetonate, alkoxide, phenoxide, nitrate, sulfate, phosphate, or chlorate; and p is 2 or 3.

5. The method of claim 1 wherein a member of the control catalyst set may be characterized by Structure II:

Structure II wherein $R^{11}$, $R^{12}$, $R^{13}$, $R^{14}$, $R^{15}$, $R^{21}$, $R^{22}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are each independently, hydrogen, an alkyl group, an alkoxy group, or a halogen atom, n ranges from about 1 to about 5;

M is a group IVB, VB, or VIB metal;

X is a halide, carboxylate, acetonate, alkoxide, phenoxide, nitrate, sulfate, phosphate, or chlorate; and p is 2 or 3.

6. The method of claim 1 wherein a member of the control catalyst set may be characterized by Structure IV:

Structure IV wherein $R^1$ is a $C_1$ to $C_{30}$ organyl group;

$R^2$ is hydrogen or a $C_1$ to $C_{30}$ organyl group consisting essentially of inert functional groups;

$R^3$ is hydrogen or a $C_1$ to $C_{30}$ organyl group consisting essentially of inert functional groups;

$R^4$ and $R^5$ are each independently a $C_1$ to $C_{30}$ organyl group consisting essentially of inert functional groups;

M is a group IVB, VB, or VIB metal;

X is a halide, carboxylate, acetonate, alkoxide, phenoxide, nitrate, sulfate, phosphate, or chlorate;

p is 2 or 3;

Q is a neutral ligand; and a ranges from 0 to 6.

7. The method of claim 1 wherein the one or more characteristics of the geometrically and energetically optimized structure of the intermediate further comprising expected positions of the constitutive atoms, the absolute and relative energies, electronic charge distributions, dipoles and higher multipole moments, vibrational frequencies, individual bond lengths, bond angles, dihedral angles, or combinations thereof.

8. The method of claim 1 wherein the mathematical relationship is a linear relationship.

9. The method of claim 1 wherein the mathematical relationship is a non-linear relationship.

10. A method of generating a predictive model comprising:
(a) identifying a control catalyst set wherein individual members of the control catalyst set range in a control characteristic, wherein the control characteristic comprises catalytic activity, catalyst productivity, catalyst selectivity, or combinations thereof and wherein a member of the control catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group;
$R^{1c}$, $R^{2c}$, $R^{3c}$, $R^{4c}$ and $R^{5c}$ are each independently hydrogen or an alkyl group;
n ranges from about 1 to about 5;
M is a group IVB, VB, or VIB metal;
X is a halide, carboxylate, acetonate, alkoxide, phenoxide, nitrate, sulfate, phosphate, or chlorate; and
p is 2 or 3;
(b) preparing molecular structures of at least one intermediate in a catalytic cycle of each member of the control catalyst set;
(c) geometrically and energetically optimizing the molecular structures of the at least one intermediate, wherein the geometrically and energetically optimized intermediate comprises 7-membered metallacycle, a 9-membered metallacycle or both;
(d) generating at least one quantitative structural descriptor of the geometrically and energetically optimized intermediate, wherein the at least one quantitative structural descriptor comprises a phosphorus-nitrogen-phosphorus (PNP) bite angle or a phosphorus-nitrogen (PN) bite angle;
(e) identifying a mathematical relationship between the at least one quantitative structural characteristic and the control characteristic;
(f) utilizing the mathematical relationship to identify at least one catalyst in a sample catalyst set having the control characteristic, wherein the at least one catalyst in the sample catalyst set forms an intermediate comprising a 7-membered metallacycle, a 9-membered metallacycle or both;
(g) contacting the identified catalyst with ethylene under conditions suitable for the production of a mixture of 1-hexene and 1-octene; and
(h) recovering the mixture of 1-hexene and 1-octene.

11. The method of claim 10 wherein the control catalyst set comprises from about 3 to about 100 members and the sample catalyst set comprises from about 3 to about 100 members.

12. The method of claim 10 wherein the quantitative structural descriptor further comprise expected positions of the constitutive atoms, the absolute and relative energies, electronic charge distributions, dipoles and higher multipole moments, vibrational frequencies, individual bond lengths, bond angles, dihedral angles, or combinations thereof.

13. The method of claim 1 wherein the one or more members of the sample catalyst set comprise a transition metal and an organic ligand, wherein the organic ligand comprises a diphosphino aminyl moiety or an $N^2$-phosphinyl amidine moiety.

14. The method of claim 13 wherein the transition metal of the control catalyst set comprises chromium and wherein the transition metal of the sample catalyst set comprises chromium.

15. The method of claim 4 wherein the one or more members of the sample catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group;
$R^{1c}$, $R^{2c}$, $R^{3c}$, $R^{4c}$, and $R^{5c}$ are each independently hydrogen or an alkyl group;
n ranges from about 1 to about 5;
M is a group IVB, VB, or VIB metal;
X is a halide, carboxylate, acetonate, alkoxide, phenoxide, nitrate, sulfate, phosphate, or chlorate; and
p is 2 or 3.

16. The method of claim 5 wherein the one or more members of the sample catalyst set may be characterized by Structure II:

Structure II wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are each independently, hydrogen, an alkyl group, an alkoxy group, or a halogen atom,
n ranges from about 1 to about 5;
M is a group IVB, VB, or VIB metal;

X is a halide, carboxylate, acetonate, alkoxide, phenoxide, nitrate, sulfate, phosphate, or chlorate; and p is 2 or 3.

17. The method of claim 6 wherein the one or more members of the sample catalyst set may be characterized by Structure IV:

Structure IV wherein $R^1$ is a $C_1$ to $C_{30}$ organyl group;

$R^2$ is hydrogen or a $C_1$ to $C_{30}$ organyl group consisting essentially of inert functional groups;

$R^3$ is hydrogen or a $C_1$ to $C_{30}$ organyl group consisting essentially of inert functional groups;

$R^4$ and $R^5$ are each independently a $C_1$ to $C_{30}$ organyl group consisting essentially of inert functional groups;

M is a group IVB, VB, or VIB metal;

X is a halide, carboxylate, acetonate, alkoxide, phenoxide, nitrate, sulfate, phosphate, or chlorate;

p is 2 or 3;

Q is a neutral ligand; and a ranges from 0 to 6.

18. The method of claim 12 wherein the at least one catalyst in the sample catalyst set comprises a transition metal and an organic ligand, wherein the organic ligand comprises a diphosphino aminyl moiety or an $N^2$-phosphinyl amidine moiety.

19. The method of claim 12 wherein the at least one catalyst in the sample catalyst set may be characterized by Structure I:

Structure I wherein $R^1$, $R^2$, $R^3$, and $R^4$ are each independently an alkyl group, a cycloalkyl group, a substituted cycloalkyl group, an aromatic group, or a substituted aromatic group;

$R^{1c}$, $R^{2c}$, $R^{3c}$, $R^{4c}$, and $R^{5c}$ are each independently hydrogen or an alkyl group;

n ranges from about 1 to about 5;

M is a group IVB, VB, or VIB metal;

X is a halide, carboxylate, acetonate, alkoxide, phenoxide, nitrate, sulfate, phosphate, or chlorate; and p is 2 or 3.

20. The method of claim 7 wherein the members of the control catalyst set and the one or more members of the sample catalyst set may be characterized by:

Structure I:

Structure I wherein $R^1$, $R^2$, $R^3$, and $R^4$ are each independently an alkyl group, a cycloalkyl group, a substituted cycloalkyl group, an aromatic group, or a substituted aromatic group;

$R^{1c}$, $R^{2c}$, $R^{3c}$, $R^{4c}$, and $R^{5c}$ are each independently hydrogen or an alkyl group;

n ranges from about 1 to about 5;

M is a group IVB, VB, or VIB metal;

X is a halide, carboxylate, acetonate, alkoxide, phenoxide, nitrate, sulfate, phosphate, or chlorate; and p is 2 or 3; or Structure II:

Structure II wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^2$, $R^{33}$, $R^{34}$, $R^{35}$, $R^{41}$, $R^{42}$, $R^{43}$, $R^{44}$, and $R^{45}$ are each independently, hydrogen, an alkyl group, an alkoxy group, or a halogen atom, n ranges from about 1 to about 5;

M is a group IVB, VB, or VIB metal;

X is a halide, carboxylate, acetonate, alkoxide, phenoxide, nitrate, sulfate, phosphate, or chlorate; and p is 2 or 3; or Structure IV:

Structure IV wherein $R^1$ is a $C_1$ to $C_{30}$ organyl group;
$R^2$ is hydrogen or a $C_1$ to $C_{30}$ organyl group consisting essentially of inert functional groups;
$R^3$ is hydrogen or a $C_1$ to $C_{30}$ organyl group consisting essentially of inert functional groups;
$R^4$ and $R^5$ are each independently a $C_1$ to $C_{30}$ organyl group consisting essentially of inert functional groups;
M is a group IVB, VB, or VIB metal;
X is a halide, carboxylate, acetonate, alkoxide, phenoxide, nitrate, sulfate, phosphate, or chlorate;
p is 2 or 3;
Q is a neutral ligand; and
a ranges from 0 to 6.

\* \* \* \* \*